United States Patent [19]
Estanove et al.

[11] Patent Number: 5,948,924
[45] Date of Patent: Sep. 7, 1999

[54] PROCESS FOR THE PREPARATION OF SUBSTITUTED ANTHRAQUINONES AND APPLICATION IN THE PREPARATION OF RHEINS

[75] Inventors: Cyril Estanove, Boulogne; François Pruvost, Quimper, both of France

[73] Assignee: Girex (Societe Anonyme), Quimper, France

[21] Appl. No.: 08/849,731

[22] PCT Filed: Oct. 31, 1996

[86] PCT No.: PCT/FR96/01714

§ 371 Date: Jul. 1, 1997

§ 102(e) Date: Jul. 1, 1997

[87] PCT Pub. No.: WO97/16404

PCT Pub. Date: May 9, 1997

[30] Foreign Application Priority Data

Nov. 2, 1995 [FR] France ................................. 95/12950

[51] Int. Cl.$^6$ .................................................. C07C 49/593
[52] U.S. Cl. ............................................................. 552/262
[58] Field of Search ............................................... 552/262

[56] References Cited

U.S. PATENT DOCUMENTS

| | | | |
|---|---|---|---|
| 3,773,801 | 11/1973 | Lang | 260/383 |
| 5,097,051 | 3/1992 | Scheeren et al. | 552/261 |

FOREIGN PATENT DOCUMENTS

| | | | |
|---|---|---|---|
| 21 44 772 | 3/1972 | Germany . | |
| 2144772 | 3/1972 | Germany | 552/262 |
| 1817767 | 5/1993 | U.S.S.R. . | |

OTHER PUBLICATIONS

Trost et al., "On the Regioselectivity of the Catalyzed and Uncatalyzed Diels–Alder Reaction", Journal of the American Chemical Society, vol. 99, No. 24, 8116–8118 (1977).
Boisvert et al., "Regiospecific Addition of Monooxygenated Dienes to Halo–Quinones", Journal of Organic Chemistry, vol. 53, No. 17, 4052–4058 (1988).
Krohn, Tetrahedron Letters, vol. 21, 3557–3560 (1980).
Jung et al., "Synthetic Approaches to Aclacinomycin and Pyrromycin Antitumour Antibiotics via Diels–Alder Reactions of 6–Alkoxy–2–pyrones: Total Synthesis of Chrysophanol, Helminthosporin and Pachybasin", J.C.S. Chem. Comm., 95–96 (1978).
Petrzilka et al., Preparation and Diels–Alder Reactions of Hetero–Substituted 1,3–Dienes, Synthesis, 753–786 (1981).
Jesaitis et al., "Juglone: An Organic Chemistry–Ecology Interaction Experiment", J. Chem. Ed., vol. 49, No. 6, 436–437 (1972).
Wakamatsu et al., "A Convenient Synthesis of Juglone Via Neutral Salcomine Oxidation", Synthetic Communications, vol. 14, No. 12, 1167–1173 (1984).
Boisvert et al, J. Org. Chem. vol. 53, pp. 4052–4059 (1988).
Nakatsubo et al, Chemical abstract vol. 99 pp. 8116–8118 (1977).
Matsuura et al, Chemical abstract, vol. 85 No. 32701, "Tetrahydroanthiaquinone", 1976.
Oda et al, Chemical abstract, vol. 90 No. 6136. "Synthesis of polycyclines", 1978.

*Primary Examiner*—John Kight
*Assistant Examiner*—Raymond Covington
*Attorney, Agent, or Firm*—Foley & Lardner

[57] ABSTRACT

A process for the preparation of substituted anthraquinones is provided. The anthraquinones can be used to prepare pharmaceutically useful rheins.

13 Claims, No Drawings

PROCESS FOR THE PREPARATION OF SUBSTITUTED ANTHRAQUINONES AND APPLICATION IN THE PREPARATION OF RHEINS

This application is a 371 of PCT FR 96/01714 filed Oct. 31, 1996.

The present invention relates to a new process for the preparation of substituted anthraquinones from 1,4-naphthoquinones and to the application of the products obtained as intermediates in the synthesis of rheins exhibiting therapeutically useful properties.

The preparation of anthraquinones, such as chrysophanol, by addition of 6-methoxy-4-methylpyrone to a naphthoquinone, such as juglone, according to the Diels-Alder reaction, has been described by M. E. Jung et al., J.C.S. Chem. Comm., 95 (1978). However, this process requires a number of stages, that is to say an addition, followed by an oxidation with silver oxide, in order to cause aromatization of the rings, and a demethylation. Moreover, the reaction involves the use of diazomethane, which has well-known disadvantages.

Synthetic routes to anthracyclinones by a cyclo-Diels-Alder addition reaction have also been described by M. Petrzilka and J. I. Grayson [Synthesis, 753 (1981)]. According to these authors, the regiospecific addition reaction of a diene with a quinone can be obtained by using a Lewis acid composed of the compound $BF_3.O(C_2H_5)_2$ as catalyst.

The process according to the present invention makes it possible to prepare substituted anthraquinones from 1,4-naphthoquinones in only two stages and with a satisfactory yield.

The anthraquinones which can be prepared by the process according to the present invention can be represented by the general formula (I) below:

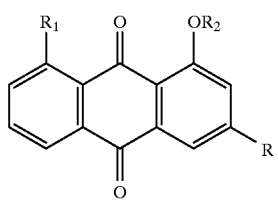

(I)

in which R represents a hydrogen atom or a linear or branched alkyl group containing 1 to 5 carbon atoms, a chloromethyl group, a —COCl group, a —COOR' group or a —CH$_2$OR' group where R' is a hydrogen atom or a linear or branched alkyl group containing 1 to 5 carbon atoms, R$_1$ represents a hydrogen atom, a hydroxyl group, a linear or branched alkoxy group containing 1 to 5 carbon atoms or an acyloxy group containing 1 to 5 carbon atoms, and R$_2$ represents a hydrogen atom or a linear or branched alkyl group containing 1 to 5 carbon atoms.

In accordance with the process of the invention, a Diels-Alder reaction is carried out between a 1,4-naphthoquinone of general formula (II):

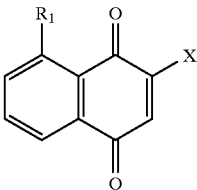

(II)

in which R$_1$ represents a hydrogen atom, a hydroxyl group, a linear or branched alkoxy group containing 1 to 5 carbon atoms or an acyloxy group containing 1 to 5 carbon atoms and X represents a hydrogen atom or a halogen atom, and an acyclic diene of formula (III):

in which R represents a hydrogen atom or a linear or branched alkyl group containing 1 to 5 carbon atoms, a chloromethyl group, a —COCl group, a —COOR' group or a —CH$_2$OR' group where R' is a hydrogen atom or a linear or branched alkyl group containing 1 to 5 carbon atoms and R$_3$ represents a linear or branched alkyl group containing 1 to 5 carbon atoms or an acyl group in which the alkyl part is linear or branched and contains 1 to 5 carbon atoms, and a saponification, aromatization and oxidation reaction is subsequently carried out.

In the above formula (II) representing the starting naphthoquinone, R$_1$ preferably represents a hydroxyl or acetoxy group and X is a hydrogen atom or a chlorine atom. In the general formula (III) representing the acyclic diene, it is preferable for R to represent a hydrogen atom or a methyl group and R$_3$ a methyl, acetyl or t-butylcarbonyl group.

The acyclic diene of formula (III) used in the reaction described above can be a butadiene derivative, such as an ester, and for example 1-acetoxy-1,3-butadiene or 1-acetoxy-3-methyl-1,3-butadiene.

Among the naphthoquinones of general formula (II), it is preferable to use juglone, represented by the formula (II) where R$_1$ represents a hydroxyl group, or 3-chlorojuglone, represented by the same formula where X is a chlorine atom. Juglone can be prepared, for example, by oxidation of 1,5-dihydroxynaphthalene in the presence of an appropriate catalyst, as described in Patent SU-1,817,767, or with chromium oxide, by the method of G. Jesaitis et al., J. Chem. Ed., 49, 436 (1972), or alternatively by oxidation by means of atmospheric oxygen in the presence of a cobalt-based catalyst, such as salcomine, according to the method of T. Wakamatsu et al., Synthetic Communications, 14, 1167 (1984).

The cyclo-Diels-Alder addition reaction between the 1,4-naphthoquinone of general formula (II) and the acyclic diene of general formula (III) is preferably carried out in a solvent, which can be chosen from hydrocarbon solvents and alcohols, such as toluene, xylene, benzene or methanol, in the presence of acetic anhydride. The acetic anhydride is preferably used in excess. According to an advantageous embodiment of the invention, the reaction is carried out in the presence of a catalytic amount of hydroquinone.

According to an alternative implementational form of the invention, the reaction is carried out in the presence of a Lewis acid which can preferably be chosen from zinc chloride and ferric chloride.

The addition reaction can be carried out at room temperature or by gently heating at a temperature of between 20 and 60° C. The reaction can also be carried out by heating at the reflux temperature of the solvent, for example at a temperature of between 60 and 130° C. approximately, depending on the solvent used.

The process in accordance with the present invention is particularly advantageous in that it makes it possible to obtain the anthraquinone, that is to say a compound with an aromatic ring, in a simple way in two stages without it being necessary to isolate intermediate compounds and without use of a compound, such as silver oxide, for bringing about the aromatization, in contrast to conventional reaction schemes.

The cycloaddition reaction provides the tetrahydroanthraquinones corresponding to the anthraquinones of formula (I) in the form of a mixture of two isomers, where the R group is in the 2 or 3 position and the $OR_3$ group is in the 4 or 1 position respectively, in variable proportions depending on the operating conditions. These tetrahydroanthraquinones can be easily converted into anthraquinones of formula (I) by saponification, oxidation and aromatization, for example by treatment with an oxidant such as N-bromosuccinimide or manganese dioxide. According to an advantageous embodiment, the saponification-oxidation-aromatization reaction is carried out directly on the mixture of the isomeric tetrahydroanthraquinones, which makes it possible to facilitate the treatment and to improve the overall yield.

The substituted anthraquinones obtained by the process according to the present invention can be used in the preparation of rheins of general formula (IV)

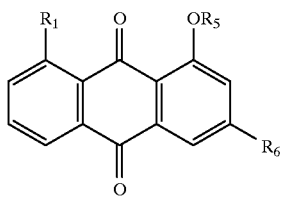

in which $R_5$ represents an acetyl group and $R_6$ represents a —$CO_2R'$ group where R' is a hydrogen atom or a linear or branched alkyl group containing 1 to 5 carbon atoms, which are obtained by carrying out an acetylation of the substituted anthraquinones of general formula (I), followed, if necessary, by an oxidation and by a purification.

These rheins are useful in human and veterinary therapeutics as active principles of medicaments, in particular as nonsteroidal anti-inflammatories in the treatment of arthritis and of osteoarthritis.

The following examples illustrate the invention in more detail without limiting the scope thereof.

EXAMPLE 1

A mixture of 0.5 g of juglone, 0.93 g of 1-acetoxy-3-methyl-1,3-butadiene and 0.9 ml of acetic anhydride in 10 ml of toluene is brought to reflux (approximately 110° C.) in a 100 ml round-bottomed flask and is maintained at reflux for 48 hours, in the presence of a catalytic amount of hydroquinone.

The progress of the reaction is monitored by thin layer chromatography. The reaction is complete when the juglone is no longer detected.

The toluene is removed by distillation under reduced pressure and the crude product obtained is chromatographed on a column of silica gel, elution being carried out with a cyclohexane/ethyl ether (80/20) mixture.

180 mg of mixture are thus obtained, which mixture is composed of 65% of 1-acetoxy-3-methyl-1,1a,4,4a-tetrahydroanthranone and 35% of 4-acetoxy-8-hydroxy-2-methyl-1,1a,4,4a-tetrahydro-anthraquinone.

The two isomers are rapidly saponified in basic medium (dilute sodium carbonate) and oxidized and aromatized using 150 mg of manganese(IV) dioxide. The two isomers are separated by chromatography on a column of silica gel. The chrysophanol thus obtained with a yield of 9% is identified by its NMR spectrum.

EXAMPLE 2

The preparation is carried out as in Example 1 but by using 5.4 ml of acetic anhydride in the toluene and by heating at reflux for 24 hours.

The reaction is complete after approximately 24 hours. The toluene is removed by distillation under reduced pressure.

200 mg of mixture are thus obtained, which mixture is composed of 65% of 1-acetoxy-8-hydroxy-3-methyl-1,1a,4,4a-tetrahydroanthraquinone and 35% of 4-acetoxy-8-hydroxy-2-methyl-1,1a,4,4a-tetra-hydroanthraquinone.

After saponification, oxidation and aromatization according to the technique described in Example 1, chrysophanol is obtained with a yield of 10%.

EXAMPLE 3

The preparation is carried out as in Example 2 but by replacing the toluene with xylene.

The reaction takes place in the same way and 200 mg of mixture are obtained, which mixture is composed of 65% of 1-acetoxy-8-hydroxy-3-methyl-1,1a,4,4a-tetrahydroanthraquinone and 35% of 4-acetoxy-8-hydroxy-2-methyl-1,1a,4,4a-tetrahydroanthraquinone.

After saponification, oxidation and aromatization according to the technique described in Example 1, chrysophanol is obtained with a yield of 10%.

EXAMPLE 4

A mixture of 0.5 g of juglone, 0.93 g of 1-acetoxy-3-methyl-1,3-butadiene and 195 mg of zinc chloride in 10 ml of toluene is brought to reflux in a 100 ml round-bottomed flask. The mixture is maintained at reflux for approximately 90 minutes, in the presence of a catalytic amount of hydroquinone.

The juglone is no longer detected by thin layer chromatography after 90 minutes.

The toluene is removed by distillation under reduced pressure and the crude product obtained is chromatographed on a column of silica gel, elution being carried out with a cyclohexane/ethyl ether (80/20) mixture.

210 mg of mixture are thus obtained, which mixture is composed of 70% of 1-acetoxy-8-hydroxy-3-methyl-1,1a,4,4a-tetrahydroanthraquinone and 30% of 4-acetoxy-8-hydroxy-2-methyl-1,1a,4,4a-tetrahydroanthraquinone.

After saponification, oxidation and aromatization according to the technique described in Example 1, chrysophanol is obtained with a yield of 11%.

EXAMPLE 5

0.5 g of juglone and 0.93 g of 1-acetoxy-3-methyl-1,3-butadiene are mixed in 10 ml of toluene in a 100 ml round-bottomed flask. The mixture is maintained at room temperature with stirring for approximately 14 hours, in the presence of a catalytic amount of hydroquinone.

The juglone is no longer detected by thin layer chromatography after 14 hours.

The toluene is removed by distillation under reduced pressure and the crude product obtained is chromatographed on a column of silica gel, elution being carried out with a cyclohexane/ethyl ether (80/20) mixture.

670 mg of mixture are thus obtained, which mixture is composed of 80% of 1-acetoxy-8-hydroxy-3-methyl-1,1a,4,4a-tetrahydroanthraquinone and 20% of 4-acetoxy-8-hydroxy-2-methyl-1,1a,4,4a-tetrahydroanthraquinone.

After saponification, oxidation and aromatization according to the technique described in Example 1, chrysophanol is obtained with a yield of 42%.

EXAMPLE 6

The reaction is carried out as in Example 4, by using 78 mg of zinc chloride but by allowing the reaction to take place at room temperature, with stirring, in the presence of a catalytic amount of hydroquinone.

Monitoring by thin layer chromatography shows that the juglone has reacted after 14 hours.

The desired product is collected after distilling off the toluene under reduced pressure and chromatography on a column of silica gel, elution being carried out with a cyclohexane/ethyl ether (80/20) mixture.

700 mg of mixture are thus obtained, which mixture is composed of 70% of 1-acetoxy-8-hydroxy-3-methyl-1,1a,4,4a-tetrahydroanthraquinone and 30% of 4-acetoxy-8-hydroxy-2-methyl-1,1a,4,4a-tetrahydroanthraquinone.

After saponification, oxidation and aromatization according to the technique described in Example 1, chrysophanol is obtained with a yield of 38%.

EXAMPLE 7

The preparation is carried out as in Example 6, but by replacing the zinc chloride with 93 mg of ferric chloride in 10 ml of toluene, at room temperature with stirring.

The starting juglone is no longer detected by thin layer chromatography after 14 hours.

After distilling off the toluene under reduced pressure, the crude product is chromatographed on a column of silica gel, elution being carried out with a cyclohexane/ethyl ether (80/20) mixture. 710 mg of mixture are thus obtained, which mixture is composed of 55% of 1-acetoxy-8-hydroxy-3-methyl-1,1a,4,4a-tetrahydroanthraquinone [sic] and 45% of 4-acetoxy-8-hydroxy-2-methyl-1,1a,4,4a-tetrahydroanthraquinone.

After saponification, oxidation and aromatization according to the technique described in Example 1, chrysophanol is obtained with a yield of 30%.

EXAMPLE 8

The preparation is carried out as in Example 5 by reacting a mixture of 0.6 g of 3-chlorojuglone and 0.93 g of 1-acetoxy-3-methyl-1,3-butadiene in 10 ml of toluene.

The juglone is no longer detected by thin layer chromatography after 14 hours, which shows that the reaction is complete.

The toluene is removed by distillation under reduced pressure and the crude product obtained is chromatographed on a column of silica gel, elution being carried out with a cyclohexane/ethyl ether (80/20) mixture.

660 mg of mixture are thus obtained, which mixture is composed of 90% of 1-acetoxy-8-hydroxy-3-methyl-1,1a,4,4a-tetrahydroanthraquinone and 10% of 4-acetoxy-8-hydroxy-2-methyl-1,1a,4,4a-tetrahydroanthraquinone.

After saponification, oxidation and aromatization according to the technique described in Example 1, chrysophanol is obtained with a yield of 46%.

EXAMPLE 9

The preparation is carried out as in Example 5 by reacting a mixture of 0.5 g of juglone and 0.83 g of 1-acetoxy-1,3-butadiene in 10 ml of toluene.

The juglone is no longer detected by thin layer chromatography after 12 hours.

The toluene is removed by distillation under reduced pressure and the crude product obtained is chromatographed on a column of silica gel, elution being carried out with a cyclohexane/ethyl ether (80/20) mixture. 660 mg of mixture are thus obtained, which mixture is composed of 80% of 1-acetoxy-8-hydroxy-1,1a,4,4a-tetrahydroanthraquinone and 20% of 4-acetoxy-8-hydroxy-1,1a,4,4a-tetrahydroanthraquinone.

After saponification, oxidation and aromatization according to the technique described in Example 1, 1,8-dihydroxyanthraquinone is obtained with a yield of 41%.

We claim:

1. A process for the preparation of substituted anthraquinones represented by the general formula (I) below

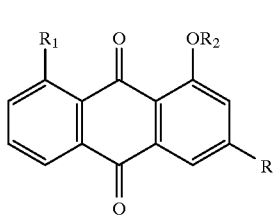

(I)

in which R represents a hydrogen atom or a linear or branched alkyl group containing 1 to 5 carbon atoms, a chloromethyl group, a —COCl group, a —COOR' group or a —CH$_2$OR' group where R' is a hydrogen atom or a linear or branched alkyl group containing 1 to 5 carbon atoms, R$_1$ represents a hydrogen atom, a hydroxyl group, a linear or branched alkoxy group containing 1 to 5 carbon atoms or an acyloxy group containing 1 to 5 carbon atoms, and R$_2$ represents a hydrogen atom or a linear or branched alkyl group containing 1 to 5 carbon atoms, comprising carrying out a Diels-Alder reaction between a 1,4-naphthoquinone of general formula (II):

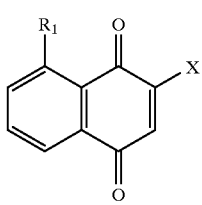

(II)

in which R$_1$ represents a hydrogen atom, a hydroxyl group, a linear or branched alkoxy group containing 1 to 5 carbon atoms or an acyloxy group containing 1 to 5 carbon atoms and X represents a hydrogen atom or a halogen atom, and an acyclic diene of formula (III):

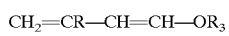

CH$_2$=CR—CH=CH—OR$_3$ (III)

in which R represents a hydrogen atom or a linear or branched alkyl group containing 1 to 5 carbon atoms, a chloromethyl group, a —COCl group, a —COOR' group or a —CH$_2$OR' group where R' is a hydrogen atom or a linear or branched alkyl group containing 1 to 5 carbon atoms and R$_3$ represents an acetyl group, in the presence of a catalytic amount of hydroquinone, followed by a saponification, aromatization, and oxidation reaction, in order to obtain the substituted anthraquinone of general formula (I).

2. A process according to claim 1, wherein the reaction is carried out in the presence of acetic anhydride.

3. A process according to claim 1, wherein the reaction is carried out in the presence of a Lewis acid.

4. A process according to claim 3, wherein the Lewis acid is chosen from zinc chloride and ferric chloride.

5. A process according to claim 1, wherein R$_1$ represents a hydroxyl or acetoxy group and X is a hydrogen atom or a chlorine atom.

6. A process according to claim 1, wherein R represents a hydrogen atom or a methyl group.

7. A process according to claim 6, wherein the diene of formula (III) is chosen from 1-acetoxy-1,3-butadiene or 1-acetoxy-3-methyl-1,3 butadiene.

8. A method for preparation of a rhein of general formula (IV)

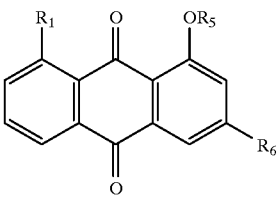

in which R$_5$ represents an acetyl group and R$_6$ represents a —CO$_2$R' group where R' is a hydrogen atom or a linear or branched alkyl group containing 1 to 5 carbon atoms, wherein an acetylation of the substituted anthraquinone of formula (I) according to claim 1 is carried out, followed, optionally, by an oxidation.

9. A process according to claim 1, wherein the reaction is carried out at room temperature.

10. A process according to claim 1, which has only two stages.

11. A process according to claim 1, wherein the 1,4-naphthoquinone is juglone or 3-chlorojuglone.

12. A process according to claim 1, wherein the reaction is carried out in the presence of an alcohol or hydrocarbon solvent.

13. A process according to claim 1, wherein the substituted anthraquinone comprises chrysophanol.

* * * * *